United States Patent [19]
Devore et al.

[11] Patent Number: 5,210,595
[45] Date of Patent: May 11, 1993

[54] SOLIDS CONCENTRATION DETECTOR

[75] Inventors: James A. Devore, Monongahela; Gary F. Meenan, Bethel Park, both of Pa.; Hayward B. Oblad, Ponca City, Okla.

[73] Assignee: Consolidation Coal Company, Pittsburg, Pa.

[21] Appl. No.: 790,835

[22] Filed: Nov. 12, 1991

[51] Int. Cl.⁵ .......................................... G01N 21/53
[52] U.S. Cl. ....................................... 356/442; 250/574
[58] Field of Search ................. 356/442, 338; 250/574

[56] References Cited

U.S. PATENT DOCUMENTS

| | | | |
|---|---|---|---|
| 3,263,553 | 8/1966 | Baruch | 356/414 |
| 3,586,862 | 6/1971 | Topol | 356/442 |
| 3,665,201 | 5/1972 | Shea et al. | 356/442 |
| 3,861,802 | 1/1975 | Belmear | 356/442 |
| 4,950,908 | 8/1990 | Oblad et al. | 250/574 |

Primary Examiner—Richard A. Rosenberger
Attorney, Agent, or Firm—Alan N. McCartney

[57] ABSTRACT

An optoelectric detector having transparent tubes separated by a thin opaque barrier with LEDs in one tube adjacent one side of the barrier and a photoconductor in the other tube adjacent to the opposite side of the barrier. The LEDs and photoconductor being in close proximity with the photoconductor with the photoconductor only receiving light emitted by the LEDs which is reflected from the solids in medium in which the detector is used.

3 Claims, 1 Drawing Sheet

SOLIDS CONCENTRATION DETECTOR

BACKGROUND OF THE INVENTION

1. Field of the Invention

This invention relates to an optoelectric detector having light emitting diodes (LEDs) separated from a photoconductor by a wall so that light from the LEDs must pass out of the detector and into a slurry to be reflected back to the photoconductor.

2. Background of the Invention

In commonly owned U.S. Pat. No. 4,950,908 there is disclosed a detector used to optimize the operation of a coal slurry processing cell. This detector has LEDs separated from a photoconductor by an opaque barrier which extends to the surface of the detector housing.

In using this detector to measure solids concentration in a coal slurry, it was discovered the glass window of the detector conducted light around the barrier and illuminated the photoconductor to a small but finite degree. This limited the extent of solids concentration measurement to about 4 wt % depending on the blackness or ash content of the solids.

Other devices such as turbidity meters are used to determine the solids concentration in a slurry. Most commercially available turbidity meters comprise two windows, usually parallel to each other, between which slurry is placed. Light passes from the source through its protective window and through the slurry. The particles in the slurry absorb or scatter some of the light and attenuate the beam which arrives at the photosensor. In order to measure slurries which contain black solids like coal above a concentration of about 2 wt %, the light must be made very bright and the path length through which the light passes must be only a few thousandths of an inch long. The brightness of the beam is limited by the size and temperature that can be tolerated in the instrument, and the transmittance path shortness is limited by particle size and flow characteristics of the slurry. Attempts to make a transmittance meter that could perform in slurries containing coals in concentrations above 2 wt % failed. The readings of the slurry in the narrow gap through which the slurry passes were unstable, and without doubt, the detector would have to be cleaned often or become plugged with solids.

The same components can be arranged with the windows placed at right angles. Light strikes the particles in the slurry and is scattered through the photosensor window and is detected. This type of meter is called a nephelometer. It is often used for measuring the cloudiness of clarified water, hence extremely dilute suspensions. Other attempts have been made to completely isolate the photoconductor from the LEDs to obtain a more accurate reading of solids concentration in a medium. U.S. Pat. Nos. 3,185,975, 3,263,553 and 3,861,802 illustrate placing barriers between the light source and light sensor. US Patents illustrate other types of detectors.

SUMMARY OF THE INVENTION

It is the purpose of this invention to provide an optoelectric detector comprising a transparent tube having sections separated by a thin wall opaque barrier, with light emitting diodes in one tube section immediately adjacent one side of the barrier and a photoconductor in the other tube section immediately adjacent the opposite side of the barrier.

It is also an object of this invention to provide a detector formed from spaced transparent tubes connected to a thin opaque barrier with LEDs on one side of the barrier and a photoconductor on the other side of the barrier, the LEDs and photoconductor being in close spaced proximity enabling the detector to be functional in dark slurries.

DESCRIPTIONS OF THE PREFERRED EMBODIMENT

The detector of this invention is the type to be utilized as a coal solids concentration detector and is utilized in the environment of the type illustrated in commonly owned U.S. Pat. No. 4,950,908; and the disclosure therein is incorporated herein by reference.

Figure 1:
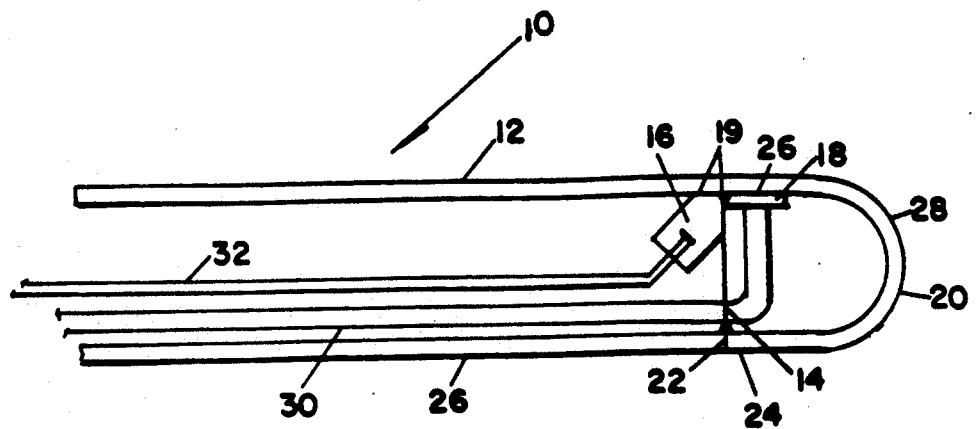
FIG. 1 is a side elevational view of the solids concentration detector of this invention.
Figure 2:
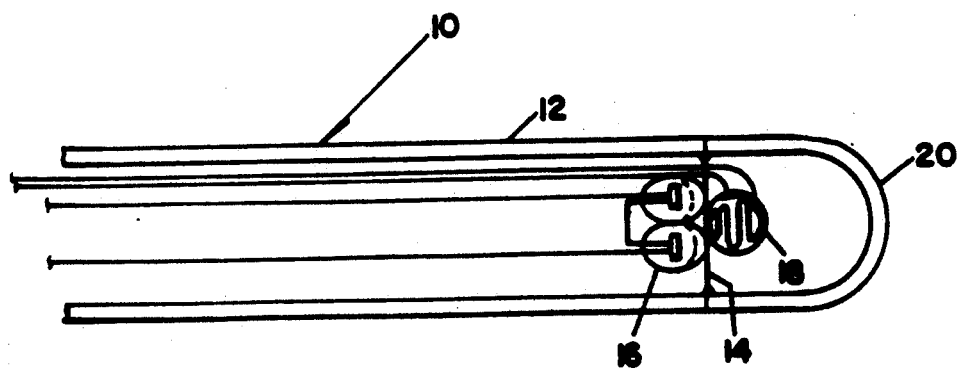
FIG. 2 is a plan view of the detector of this invention.

The detector 10 consists of a 1 inch diameter glass test tube 12, a 1 inch diameter by 0.001 inch thick stainless steel disc 14, two high intensity red LEDs 16, and a photoconductor 18. The glass tube 12 was cut perpendicularly to the axis with a diamond saw about 1 inch from the closed end 20. The cut ends 22, 24 of the tube were polished until flat. The photoconductor 18 was glued onto the inner wall 26 of the shorter piece 28 of the glass tube, the disc 14 was glued onto the cut and polished end 24, and the longer piece 26 was also glued onto the other side of the stainless disc 14. The LEDs 16 were modified to fit closer together and to project light above the photoconductor by grinding flat surfaces 19 in the sides of the LED cases. The LEDs were then mounted, using glue, onto the disc 14 directly opposite the photoconductor 18. The glass/metal interfaces were joined such that there was no glue around the outside of the joint, and that metal was interposed between all glass parts of the cut tube. Wires 30 to the photoconductor were passed down the tube and through two small holes which were drilled in the stainless steel disc. Wires 32 which carry electrical current to the LEDs were also passed down the tube and connected to the terminals. The LEDs were connected in series. The arrangement and assembly of the components were shown in FIGS. 1 and 2. It should be appreciated that other geometric configurations other than tubes could be used to accomplish the same objective.

This detector differs from previous designs because the photoconductor is completely isolated from the LEDs. Although there has always been an opaque barrier between the light sources and photosensors in earlier units (see FIG. 3 of U.S. Pat. No. 4,950,908), the glass window conducted light around the barrier and illuminated the photoconductor to a small but finite degree. This limited the extent of solids concentration measurement to about 4 wt % depending on the blackness or ash content of the solids. Since no light can arrive at the photoconductor in the unit of this invention without passing through the slurry, its sensitivity to extremely small illumination can be exploited.

In the detector of this invention, since the LEDs and photoconductor are closely spaced and only reflected light from the slurry solids is picked up by the photoconductor, then only the change in amount of particles is sensed by the photoconductor, and thus the detector is only sensing the change in solids concentration.

Thus an optoelectronic detector was developed that can measure higher concentrations of fine coal solids in slurries. Whereas most commercial turbidity meters can only measure solids concentrations of coal up to about 2 wt % and units as disclosed in U.S. Pat. No. 4,950,908 ceased working at about 4 wt % this unit has measured extremely black slurries containing 10 wt % solids having an ash content of 28 wt %.

We claim:

1. An optoelectric detector responsive to the change in solids concentration in a coal slurry comprising:
   a. a pair of open ended spaced sections with transparent walls;
   b. a thin wall opaque barrier attached to the open end of each spaced section with said spaced sections being separated by said barrier and not in contact with one another;
   c. a light source enclosed in one spaced section adjacent said barrier for transmitting light into the slurry;
   d. a photoconductor enclosed in the other spaced section adjacent said barrier for receiving reflected light from said slurry; and
   e. said barrier attachment to the spaced sections prohibiting light transmittance from one section to the other through the spaced sections so that only light reflected from the slurry solids is transmitted to the photoconductor.

2. The optoelectric detector of claim 1 wherein said light source are LEDs which are shaped to the contour of the sections which permits the diodes to be in close proximity to the photoconductor so that emitted light can travel short distances into the slurry to be reflected, enabling the detector to be functional in dark slurries.

3. The optoelectric detector of claim 1 wherein each of the spaced sections are tubular in geometric configuration.

* * * * *